United States Patent [19]
Choi

[11] Patent Number: 5,955,471
[45] Date of Patent: Sep. 21, 1999

[54] TETRAHYDROISOQUINOLINEALKANOL DERIVATIVES AND PHARMACEUTICAL COMPOSITIONS CONTAINING SAME

[75] Inventor: Yong Moon Choi, Towaco, N.J.

[73] Assignee: SK Corporation, Fairfield, N.J.

[21] Appl. No.: 08/995,645

[22] Filed: Jan. 13, 1998

[51] Int. Cl.$^6$ .................. A61K 31/47; C07D 217/00; C07D 217/16

[52] U.S. Cl. .................. 514/307; 546/139; 546/144; 546/149; 546/146

[58] Field of Search ............... 546/144, 139; 514/307

[56] References Cited

U.S. PATENT DOCUMENTS

| | | | |
|---|---|---|---|
| 3,308,128 | 3/1967 | Richard | 260/288 |
| 3,449,360 | 6/1969 | Renat | 260/313.1 |
| 5,246,943 | 9/1993 | Blankley et al. | 514/307 |

FOREIGN PATENT DOCUMENTS

| | | |
|---|---|---|
| 564193 | 6/1993 | European Pat. Off. |
| 2266529 | 11/1993 | United Kingdom |
| WO9320099 | 10/1993 | WIPO |
| WO9413661 | 6/1994 | WIPO |
| WO9413664 | 6/1994 | WIPO |
| WO9617610 | 6/1994 | WIPO |
| WO9533727 | 12/1995 | WIPO |
| WO9616982 | 6/1996 | WIPO |

OTHER PUBLICATIONS

Kametani et al., (CA 70:3790, Yakugaku Zasshi (1968), 88 (5), 573–582).
CA 61:11970c.
Gafurov, M. B., (Uzb. Khim. Zh. (1988), (5), 15–17).
Gray, Allen P., (CA71:81213, DE 1806900).

Primary Examiner—Jose' G. Dees
Assistant Examiner—Sabiha Qazi
Attorney, Agent, or Firm—Gibbons, Del Deo, Dolan, Griffinger & Vecchione

[57] ABSTRACT

The present invention provides novel 1,2,3,4-tetrahydroisoquinoline carbamate and thiocarbamate derivatives represented by Formula I

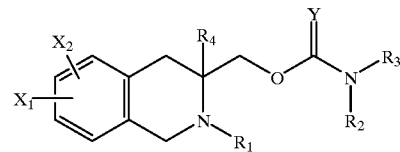

wherein:

$X_1$ and $X_2$ are the same or different from each other and independently represent a a member selected from the group consisting of hydrogen, alkyl, alkoxy, thioalkoxy, halogen, hydroxy, nitro and trifluorocarbon;

Y is a member selected from the group consisting of oxygen and sulfur;

$R_1$ is a member selected from the group consisting of hydrogen, alkyl, arylalkyl, and CONHR' where R' is selected from the group consisting of hydrogen, alkyl, arylalkyl and aryl;

$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;

$R_4$ is a member selected from the group consisting of hydrogen or lower alkyl; and nontoxic pharmacologically acceptable salts thereof.

Compounds are useful in the treatment of central nervous system disorders, including depression.

49 Claims, No Drawings

TETRAHYDROISOQUINOLINEALKANOL DERIVATIVES AND PHARMACEUTICAL COMPOSITIONS CONTAINING SAME

FIELD OF THE INVENTION

The present invention relates to a novel class of pharmaceutically active compounds and compositions for treating diseases of the central nervous systems, including depressive states and cognitive disorders.

BACKGROUND OF THE INVENTION

Depression is the primary characteristic of mood or affective disorders. It is estimated that in the U.S. 1 out 10 persons in the general population will suffer from depression during their lifetime. Although there are many drug therapies available, the current treatment is only effective in 70% of the patient population. There is still a lack of adequate treatment for the remaining 30% and more new drug therapies are urgently needed. Due to these facts, it has remained a major challenge to medicinal chemists to develop a new class of antidepressants.

It has now been discovered that hydroxyalkyltetrahydroisoquinoline derived carbamate and thiocarbamate compounds have demonstrated significant activity with respect to central nervous systems models, including depression, with excellent toxicological profiles.

SUMMARY OF THE INVENTION

The present invention relates to novel 1,2,3,4-tetrahydroisoquinoline carbamate and thiocarbamate derivatives represented by Formula I

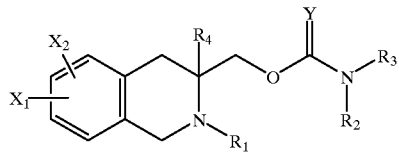

I or pharmaceutically acceptable salts thereof wherein $X_1$, $X_2$, Y, $R_1$, $R_2$, $R_3$, and $R_4$ are as defined below. The present invention is an advance in the art since it provides a new class of pharmaceutically active compounds, which are useful in the treatment of central nervous system diseases, including depression. The invention also includes a pharmaceutical composition comprising a central nervous system effective amount of a compound of Formula I above in admixture with a pharmaceutically acceptable carrier or excipient and a method for treatment in a mammal suffering therefrom which comprises administering to said mammal the above pharmaceutical composition in unit dosage form.

In biological assays, the compounds of Formula I have been shown to possess activity in central nervous system models, including depression and monoamine oxidase (MAO) inhibitory properties. The novel compounds are thus useful for treating a subject afflicted with central nervous system disorders, including depression.

DETAILED DESCRIPTION

The products of this invention are compounds of the following general formula I:

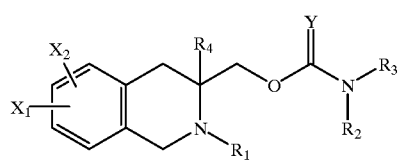

I wherein:
$X_1$ and $X_2$ are the same or different from each other and independently represent a member selected from the group consisting of hydrogen, alkyl, alkoxy, thioalkoxy, halogen, hydroxy, nitro and trifluorocarbon;
Y is a member selected from the group consisting of oxygen and sulfur;
$R_1$ is a member selected from the group consisting of hydrogen, alkyl, arylalkyl, and CONHR' where R' is selected from the group consisting of hydrogen, alkyl, arylalkyl and aryl;
$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;
$R_4$ is a member selected from the group consisting of hydrogen or lower alkyl; and
nontoxic pharmacologically acceptable salts thereof.

Certain compounds of the present invention possess one or more chiral centers and each center exists in the R or S configuration. The present invention includes all enantiomeric and diastereomeric forms, as well as the appropriate mixtures thereof Set forth below are definitions of the radicals covered by Formula I.

The term "alkyl" means a straight or branched hydrocarbon radical having from one to eight carbon atoms and includes, for example, methyl, ethyl, n-propyl, isopropyl, n-butyl, sec-butyl, isobutyl, tert-butyl, n-pentyl, n-hexyl, and the like except where specifically stated otherwise.

The term "halogen" includes fluorine, chlorine, bromine, and iodine; the more preferred halogens are fluorine and chlorine.

The term "alkoxy" refers to an alkyl radical attached to the remainder of the molecule by oxygen; this includes, but is not limited to methoxy, ethoxy, and propoxy groups.

The term "thioalkoxy" refers to an alkyl radical attached to the remainder of the molecule by sulfur; this includes, but is not limited to, thiomethoxy, thioethoxy, and thiopropoxy groups.

The term "cyloalkyl" refers to a cyclic group of from three to six carbon atoms; preferred cycloalkyls are cyclopentyl and cyclohexyl.

The term "aryl" refers to aromatic hydrocarbons such as phenyl, napthyl, and the like and may be unsubstituted or substituted selected from alkyl, such as methyl or ethyl, alkoxy, such as methoxy or ethoxy, halogen, $NO_2$ and $SCH_3$.

The term "arylalkyl" is as defined above for alkyl and for aryl. Such groups include, but are not limited to, $PhCH_2$.

Included within this invention are the non-toxic pharmaceutically acceptable salts of the instant product I. Suitable salts include the acid addition salts of the compound of Formula I, including salts derived from nontoxic inorganic acids, such as hydrochloric, nitric, phosphoric, sulfuric, hydrobromic, hydriodic, phosphorous, and the like, as well as the salts derived from nontoxic organic acids, such as, acetic acid, propionic acid, glycolic acid, lactic acid, pyruvic acid, oxalic acid, malonic acid, succinic acid, maleic acid, humeric acid, tartaric acid, citric acid, benzoic acid, cinnamic acid, salicyclic acid, mandelic acid, methanesulfonic acid, ethanesulfonic acid, benzenesulfonic acid, toluenesulfonic acid, and the like.

The acid addition salts of said basic compounds are prepared by contacting the free base form with a sufficient amount of the desired acid to produce the salt in the conventional manner. The free base form may be regenerated by contacting the salt form with a base and isolating the free in base the conventional manner.

A preferred embodiment of this invention are compounds according to Formula (II) wherein Y is oxygen:

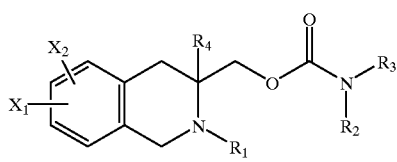

II and wherein:

$X_1$ and $X_2$ are the same or different from each other and independently represent a member selected from the group consisting of hydrogen, alkyl alkoxy, thioalkoxy, halogen, hydroxy, nitro and trifluorocarbon;

$R_1$ is a member selected from the group consisting of hydrogen, alkyl, arylalkyl and CONHR' where R' is selected from the group consisting of hydrogen, alkyl, arylalkyl and aryl;

$R_2$ and $R_3$ are the same or different from each other and independently represent a member selected from the group consisting of hydrogen, alkyl, arylalkyl and cycloalkyl, or $R_2$ and $R_3$ may form a 5 to 7-membered ring together with the nitrogen atom to which they are bonded;

$R_4$ is a member selected from the group consisting of hydrogen or lower alkyl; and nontoxic pharmacologically acceptable salts thereof.

Another preferred embodiment of this invention are compounds according to Formula (III) wherein Y is sulfur:

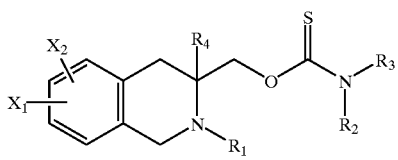

III and wherein:

$X_1$ and $X_2$ are the same or different from each other and independently represent a member selected from the group consisting of hydrogen, alkyl, alkoxy, thioalkoxy, halogen, hydroxy, nitro and trifluorocarbon;

$R_1$ is a member selected from the group consisting of hydrogen, alkyl, arylalkyl, and CONHR' where R' is selected from the group consisting of hydrogen, alkyl arylalkyl and aryl;

$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;

$R_4$ is a member selected from the group consisting of hydrogen or lower alkyl; and nontoxic pharmacologically acceptable salts thereof.

Another preferred embodiment of this invention resides in the enantiomerically enriched compounds of Formula (IV):

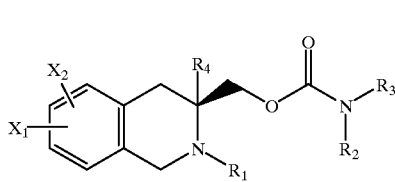

IV wherein:

$X_1$ and $X_2$ are the same or different from each other and independently represent a member selected from the group consisting of hydrogen, alkyl, alkoxy, thioalkoxy, halogen, hydroxy, nitro and trifluorocarbon;

$R_1$ is a member selected from the group consisting of hydrogen, alkyl, arylalkyl, and CONHR' where R' is selected from the group consisting of hydrogen, alkyl, arylalkyl and aryl;

$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;

$R_4$ is a member selected from the group consisting of hydrogen or lower alkyl; and nontoxic pharmacologically acceptable salts thereof Still another preferred embodiment of this invention resides in the enantiomerically enriched compound of Formula (V):

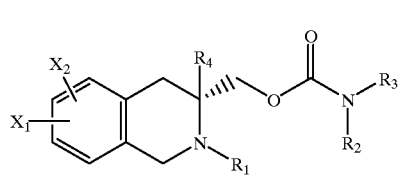

V wherein:

$X_1$ and $X_2$ are the same or different from each other and independently represent a member selected from the group consisting of hydrogen, allyl, alkoxy, thioalkoxy, halogen, hydroxy, nitro and trifluorocarbon;

$R_1$ is a member selected from the group consisting of hydrogen, alkyl, arylalkyl, and CONHR' where R' is selected from the group consisting of hydrogen, alkyl, arylalkyl and aryl;

$R_2$ and $R_3$ are the same or different from each other and independently represent a member selected from the group consisting of hydrogen, alkyl arylalkyl, and cycloalkyl, or $R_2$ and $R_3$ may form a 5 to 7-membered ring together with the nitrogen atom to which they are bonded;

$R_4$ is a member selected from the group consisting of hydrogen or lower alkyl; and nontoxic pharmacologically acceptable salts thereof Enantiomerically enriched compounds refer to compounds wherein one enantiomer form of the compound predominates over the other enantiomeric form. Preferably, one of the enantiomers predominates to the extent of 90% or greater, and most preferably, about 98% or greater.

The subject invention provides compounds of Formula I suited for treating a subject afflicted with central nervous system disorders, including depression, Parkinson's disease, a memory disorder, cognitive disorder, dementia, hyperactive syndrome, a neurodegenerative disease, an attention deficit disorder, schizophrenia, obesity, Alzheimers Disease, 2 to reaction with carbonyl diimidazole (CDI) or phosgene in the presence of amine base followed by aminolysis with $R_2R_3NH$ to yields the carbamate (compound 3). Removal of the benzyloxycarbonyl group, a nitrogen protecting group, is achieved through hydrogenolysis in the presence of the hydrogenation metal catalyst such as palladium-carbon (Pd—C) to afford the carbamate product (compound 4). The pharmaceutically acceptable salt of the product, such as the HCl salt, can be obtained by treatment of the product with HCl. Scheme I illustrates preparation of the S form of the product. It should be noted that the stereochemistry of the compounds 4 and 5 depend on the stereochemistry of the starting material compound 1. If one starts out with the R form of the starting material, the product obtained will be the R form.

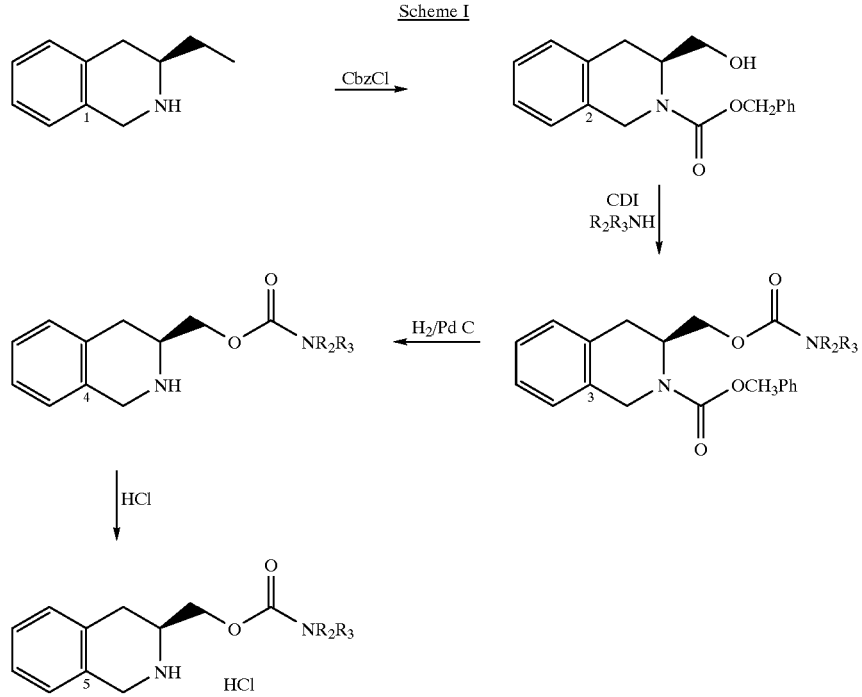

Scheme I panic attacks, pain, smoking cessation, anxiety, epilepsy, stroke or withdrawal symptoms.

Synthesis

In general, the compounds of the present invention can be prepared as illustrated in Schemes I to III. For illustrative purpose, the instance where $X_1$ and $X_2$ are hydrogen is shown.

In Scheme I, treatment of 3-hydroxymethyl-1,2,3,4-tetrahydroisoquinoline (compound 1) with a nitrogen protecting group such as benzyl chloroformate (CbzCl) yields N-benzyloxycarbonyl-3-hyroxymethyl-1,2,3,4-tetrahydroisouinoline (compound 2). Subjecting compound In Scheme II, treatment of 3-hydroxymethyl-1,2,3,4-tetradroisoquinoline (compound 6) with nitrogen protecting group such as di-tert-butyl dicarbonate or ($BOC_2O$) or 2-(tert-butoxycarbonyloxyimino)-2-phenylacetonitile (BOC-ON) affords N-BOC protected compound N-t-butyloxycarbonyl-3-hydroxymethyl-1,2,3,4-tetrahydroisoquinoline (compound 7). Treating compound 7 with sodium hydride, carbon disulfide, methyl iodide and followed by treating the resulting intermediate with amine $R_2R_3NH$ yields the compound 8. The protecting group in compound 8 is deprotected by an aqueous acid such as aqueous hydrochloric acid to yield the thiocarbamate product 9. The salt is formed by treatment with a pharmaceutically acceptable acid such as HCl to yield the hydrochloride of the thiocarbamate product 10.

Scheme II

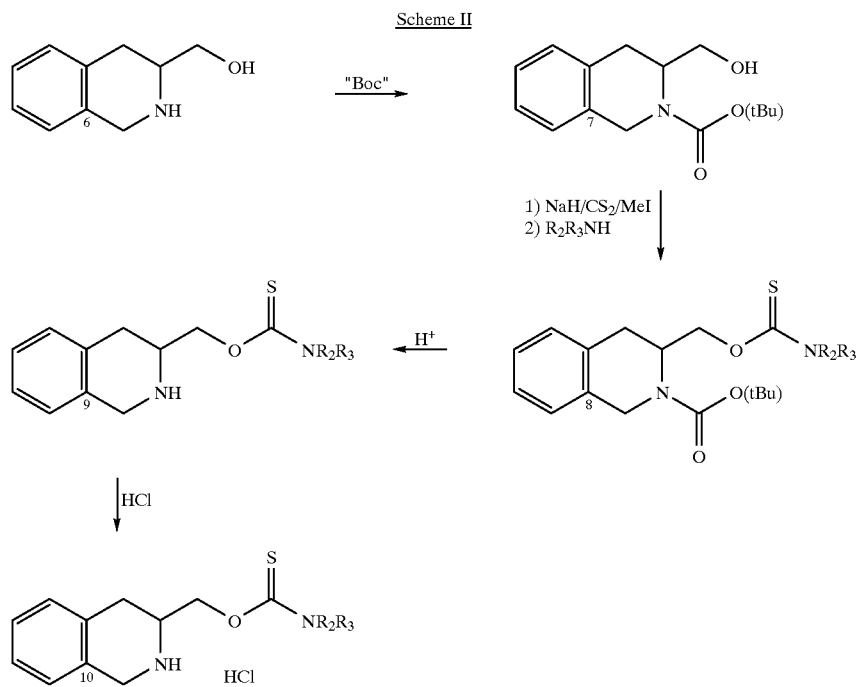

In Scheme III, treatment of (S)-3-hydroxymethyl-N-methyl-1,2,3,4,-tetrahydroisoquinoline (compound 11) with carbonyl diimidazole (CDT), followed by amine $R_2R_3NH$ yields the carbamate product compound 12. Likewise, using a similar method, compound 14 can be converted to carbamate compound 15. Treatment of (S)-3-hydroxymethyl-N-methyl-1,2,3,4,-tetrahydroisoquinoline (compound 11) with sodium hydride, carbon disulfide, and methyl iodide, followed by treatment with amine, $R_2R_3NH$, yields the thiocarbamate product 13. Likewise, using a similar method, compound 14 can be converted to thiocarbamate compound 16.

Scheme III

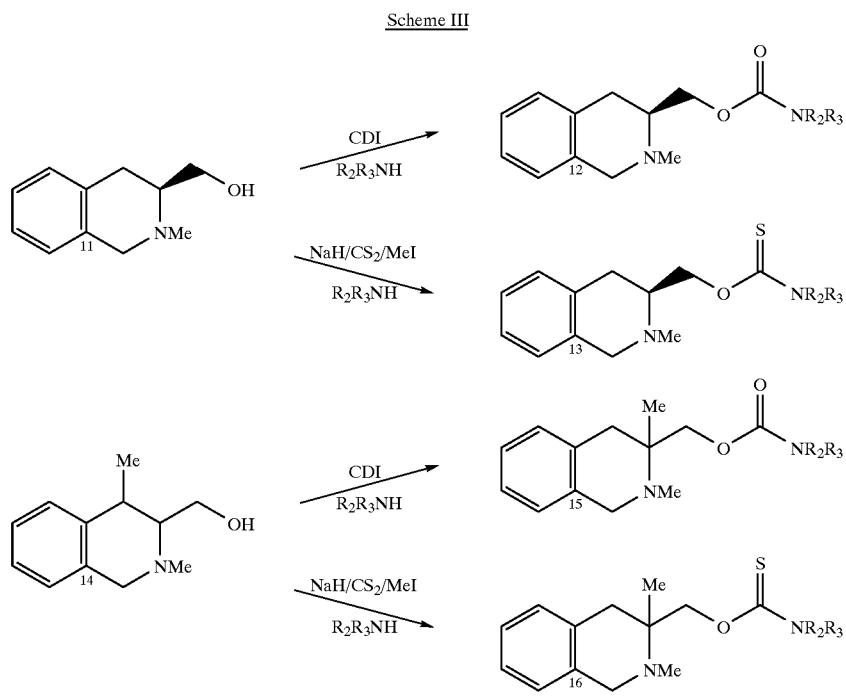

Representative compounds of Formula I are presented in Table 1.

TABLE I

Examples of Compounds

I

| Form | $X_1, X_2$ | Y | $R_1$ | $R_2$ | $R_3$ | $R_4$ |
|---|---|---|---|---|---|---|
| S | 6-Cl | O | Me | H | H | H |
| S | H | O | Et | H | H | H |
| S | H | O | $CH_2Ph$ | H | H | H |
| S | 7-$NO_2$ | O | H | H | H | H |
| RS | 7,8-$(Cl)_2$ | O | H | H | H | H |
| S | 6,7-$(OMe)_2$ | O | H | H | H | H |
| S | 6-F | O | H | H | H | H |
| S | 6-OMe | O | H | H | H | H |
| R | 6-Cl | O | Me | H | H | H |
| RS | 6-Cl | O | Me | H | H | H |
| S | H | O | Et | Me | Me | H |
| S | H | O | Et | Me | Me | Me |
| S | 6-Cl | S | Me | H | H | H |
| S | H | S | Et | H | H | H |
| S | H | S | $CH_2Ph$ | H | H | H |
| S | 7-$NO_2$ | S | H | H | H | H |
| RS | 7,8-$(Cl)_2$ | S | H | H | H | H |
| R | 6-Cl | S | Me | Me | H | H |
| RS | 6-Cl | S | Me | Me | H | Me |

Formulation

Formulation: The products (I) of this invention may be employed as the active ingredient in a variety of pharmaceutical compositions in admixture with a pharmaceutically acceptable solid or liquid diluent or carrier. Pharmaceutically acceptable diluents or carriers include any non-toxic substance which, when mixed with a product of this invention, renders it more suitable for administration either orally, intravenously or intermuscularly. In utilizing the compounds of the present invention for therapeutic use, it is preferred that they be administered orally.

Typical of the intended diluents or carriers are solid, liquid and semi-solid diluents and carriers such as paraffins, vegetable oils, mannitol, sucrose, glucose or sterile liquids such as water, saline, glycols and oils of a petroleum, animal, vegetable or synthetic origin as, for example, peanut oil, mineral oil and sesame oil. Moreover, the composition may be enhanced by including other useful ingredients such as stabilizers, binders, antioxidants, preservatives, lubricators, suspending agents, viscosity aids or flavoring agents and the like.

Dosage: The dose to be administered depends to a large extent upon the condition being treated and the weight of the host; however, a general daily dosage may consist of from about 0.1 mg to 500 mg. of active ingredient per kilogram of body weight which may be administered in a single dose or multiple doses. A total preferred daily dose lies in the range of from about 0.1 mg to 50 mg of active ingredient per kilogram of body weight.

Unit Dosage Forms: The compositions of this invention may be administered parenterally or orally in solid and liquid oral unit dosage form as, for example, in the, form of tablets, capsules, powders, suspensions, solutions, syrups, sustained release preparations and fluid injectable forms such as sterile solutions and suspensions. The term "unit dosage form" as used in this specification refers to physically discrete units which are administered in single or multiple dosages, each unit containing a predetermined quantity of active ingredient in combination with the required diluent, carrier or vehicle.

Solid Tablets: Hard tablets are prepared by combining the active ingredient, suitably comminuted, with a diluent such as starch, sucrose, kaolin or calcium phosphate and a lubricant. Optionally, the compositions may contain stabilizers, anti-oxidants, preservatives, suspending agents, viscosity aids, flavoring agents and the like. The composition is pressed into tablets and a protective coating of shellac, wax, sugar or polymeric material is added. If desired, dyes can also be included to provide a color-code means for distinguishing between different dosages.

Chewable Tablets: This unit dosage form is prepared by combining the active ingredient with a pharmaceutically acceptable orally ingestible solid carrier and a gum base. If desired, the composition may also contain flavors, binders, lubricants and other excipients.

Soft Capsule: Soft gelatin capsules are prepared by dissolving the active ingredient in a pharmaceutically acceptable oil such as peanut oil, sesame oil or corn oil together with glycerine and water.

Hard Capsule: Hard gelatin capsules may be prepared by mixing the active ingredient with lactose and magnesium stearate and placing the mixture in a No. 3 gelatin capsule. If desired, a glidant such as colloidal silica may also be added to improve flow properties and a distintegrating or solubilizing agent may be included to improve the availability of the medicament upon ingestion.

Liquids: Syrups, elixirs and suspensions can be prepared in unit dosage form so that the compositions can be administered by the teaspoonful. Syrups are prepared by dissolving the compounds in a suitably flavored aqueous sucrose solution, whereas, elixirs are prepared by combining the active ingredient with non-toxic alcoholic vehicles. Suspensions are obtained by mixing a dry powder containing the active ingredient in water with a minor amount of a suspending agent, a flavoring agent, a sweetener such as sugar and a preservative if necessary.

Parenteral: Unit dosage forms suitable for parenteral administration are prepared by suspending or dissolving a measured amount of the active ingredient in a non-toxic liquid vehicle suitable for injection such as an aqueous or oleaginous medium and sterilizing the resulting mixture. Alternatively, a measured amount of the active ingredient may be placed in a vial as a discrete entity and the vial and its contents can be sterilized and sealed. If desired, an accompanying vial containing an appropriate vehicle for admixture with said active ingredient can also be provided so that the contents of both vials can be combined and mixed for administration purposes immediately prior to use.

Topical: Powders and other solid unit dosage forms can be formulated by combining an active ingredient of this invention with a suitable carrier such as talc, bentonite, silicic acid, polyamide powder, animal and vegetable fats, wax, paraffins, starch, tragacanth, cellulose derivatives, polyethylene glycols, silicones and zinc oxide or mixtures thereof. Liquid and semi-liquid formulations, on the other hand can be prepared in the form of suspensions, solutions, ointments, pastes, creams and gels by combining an active ingredient with such carriers as polyethylene glycol, vegetable and mineral oils, alcohols such as isopropanols and the like. In addition to the aforementioned carriers the formulations can also include such other excipients as emulsifiers, preservatives, colorants, perfumes and the like.

Biological Assay Methods

The compounds of Formula I are of value in treatment of a wide variety of central nervous system conditions.

The head-twitch response of mice is initiated by a variety of 5-HT mimetic drugs. The test was conducted in a manner similar to the procedure described by Heal, D. J., Philpot, J, O'Shaughnessy, K. M. and Davies, C. L.: The influence of central noradrenergic function on 5-HT-mediated head-twitch responses in mice: Possible implications for the actions of antidepressant drugs. Psychopharmacology 89: 414–420, 1986, The head-twitch consisted of a characteristic rotation of the head, neck and shoulders of the mice. The test drug or vehicle was given by oral gavage. Thirty minutes later all animals were pretreated with carbidopa (25 mg/kg ip). Fifteen minutes following carbidopa administration, the mice were injected with 100 mg/kg ip of L-5-hydroxytryptophan (5-HTP). The animals were then left for 30 minutes before measurement of the head-twitch response in the following 2-minute period. For calculation of percent (%) response increase, the difference in drug head twitch number versus the control vehicle head twitch number is divided by the control head twitch and multiplied by 100.

| Head-Twitch Test | | |
|---|---|---|
| Example No. | Dose (mg/kg, oral) | % Response Increase |
| 3 | 1 | 238 |
| 4 | 15 | 258 |
| 5 | 3 | 144 |
| 8 | 1 | 77 |
| 14 | 8 | 42 |

Behavior Despair (Forced Swimming) test, a well known pharmacological screening method for depression, was conducted similary to the test described by Porsolt, R. D., Bertin, A and Jalfre, M.: Behavior despair in mice: A preliminary screening test for antidepressants. Arch. Int. Pharmacodyn. Ther. 229: 327–336, 1977.

Mice were dosed intraperitoneally (ip) with either test compound or vehicle. One hour later each animal was placed in a 1500 mL glass beaker containing water at room temperature. Mice were kept in the water for a period of 15 minutes and the duration of immobility observed within the 15-minute test period was recorded. A mouse was judged to be immobile if it floated motionlessly in the water making only those movements necessary to keep its head above the water. For calculation of percent (%) reduction in immobility time, the difference in immobility time for control vehicle versus the drug is divided by the immobility time of the control vehicle and multiplied by 100.

Rats were pre-swam for 10 minutes the day before the test in 4000 mL glass cylinders containing water at 25° C. On the following day, rats were dosed orally (po) with either test compound or vehicle. One hour later each animal was placed in a glass cylinder and, following a 2-minute pretest, immobility was recorded for a 4-minute test period. For calculation of percent (%) reduction in immobility time, the difference in immobility time for control vehicle versus the drug is divided by the immobility time of the control vehicle and multiplied by 100.

| Behavior Despair Test | | |
|---|---|---|
| Example No. | Dose (mg/kg) | % Reduction |
| 3 | 60 (po) | 83 |
| 18 | 30 (ip) | 33 |
| 16 | 30 (ip) | 56 |
| 17 | 30 (ip) | 46 |

The MAO-A activities in vitro were measured using Rat liver mitochondrial membranes as the source of the enzyme, according to a modified method of S. Otsuka & Y. Kobayashi: A Radioisotopic Assay for Monoamine Oxidase Determinations in Human Plasma. Biochem. Pharmacol. 13: 995–1006 (1964)

Rat liver mitochondrial membranes are preincubated with drug or vehicle, and subtype selective blocker (300 nM deprenyl to block the B type of MAO) for 60 minutes at 37° C. in 100 mM $KPO_4$ (pH 7.2). $[^{14}C]$ Serotonin (45–60 Ci/mmol) is then added and incubated for 10 minutes. The reaction is stopped by the addition of 0.5 ml of 2M citric acid. Radioactive product is extracted into a toluene/ethyl acetate fluor and compared to control values by scintillation spectrophotometry in order to ascertain any interactions of test compounds with MAO-A.

| MAO-A Inhibiting Activity at 10 uM | |
|---|---|
| Example No. | % Inhibition |
| 3 | 97.7 |
| 4 | 63.9 |

In addition, the compounds of the present invention have a reduced level of toxicity and a high safety level, so that the present invention is also highly valuable from these viewpoints.

The results obtained show that the compounds of Formula I may be suited for treating a subject afflicted with central nervous system disorders, including depression, Parkinson's disease, a memory disorder, cognitive disorder, dementia, hyperactive syndrome, a neurodegenerative disease, an attention deficit disorder, schizophrenia, obesity, Alzheimers Disease, panic attacks, pain, smoking cessation, anxiety, epilepsy, stroke or withdrawal symptoms.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

The following examples are illustrative of the instant invention; they are not intended to limit its scope in any way.

EXAMPLE 1

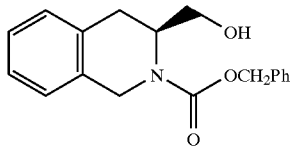

(S-N-benzyloxycarbonyl-3-hydroxymethyl-1,2,3,4-tetrahydroisoquinoline

To a stirred mixture of (S)-3-hydroxymethyl-1,2,3,4-tetrahydroisoquinoline (10 g) and sodium bicarbonate (15.5 g) in tetrahydrofuran (50 mL) was added dropwise benzyl chloroformate (9.7 mL) at 5° C. The reaction was stirred for 2 hours at room temperature, and worked up by adding ethyl acetate, washing with brine and concentrating in vacuo. The resulting concentrate was purified by flash chromatography to yield the product (17.9 g) as an oil.

$^1$H-NMR (300 Mhz, CDCl$_3$) δ: 2.48 (OH), 2.85 & 3.05 (m, 2H), 3.58 (m, 2H), 4.30–4.85 (m, 3H), 5.22 (s, 2H), 7.05–7.50 (m, 9H).

EXAMPLE 2

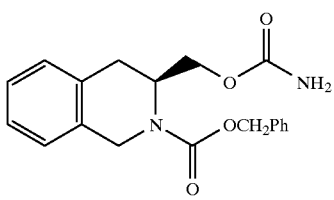

(S)-N-benzyloxycarbonyl-3-carbamoyloxycarbonyl-1,2,3,4-tetrahydroisoquinoline 25

To (S)-N-benzyloxycarbonyl-3-hydroxymethyl-1,2,3,4-tetrahydroisoquinoline(1 g) in tetrahydrofuran (5 mL) was added carbonyl diimidazole (0.6 g) and stirred for 45 minutes. Ammonium hydroxide (30%, 5 mL) was added and after overnight stirring, the reaction mixture was extracted with ethyl acetate. The extract was washed with water, 0.5 N HCl, concentrated and recrystallized from ethanol to yield the product as a white solid (0.67 g). Melting point 136.0–137.9° C.

$^1$H NMR (300 MHz, DMSO-d$_6$) δ: 2.75–3.00 (m, 2H), 3.85 (m, 2), 4.30 (m, 1H), 4.60–4.75 (2H), 5.15 (s, 2H), 6.52 (s, 2H), 7.20–7.40 (m, 9H).

EXAMPLE 3

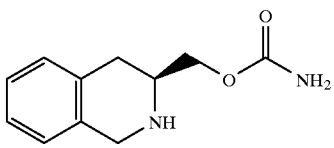

(S)-3-Carbamoyloxymethyl-1,2,3,4-tetrahydroisoquinoline (S)-N-benzyloxycarbonyl-3-carbamoyloxycarbonyl-1,2,3,4-tetrahydroisoquinoline (7 g) in methanol (150 mL) was hydrogenated at 40 psi at 40° C. in the presence of 10% palladium-carbon (2.2 g) for 1 hour. The mixture was filtered through celite and the filtrate was concentrated and recrystallized from ethanol to yield product as a solid (2.99 g). Melting point. 152–153° C.

$^1$H NMR (300 Mhz, DMSO-d$_6$) δ: 2.38 (s, br, 1H), 2.57 (m, 2H), 2.79 (dd, J=16.2, 3.8, 1H), 3.12 (m, 1H), 4.07 (m, 4H), 6.80 (s, br, 2H), 7.22 (m, 4H) [α]$_D^{25}$=−81.6 (c=1.0, MeOH)

The product was treated with HCl—isopropanol to yield the product hydrochloride.

Melting point 203–205° C. $^1$H NMR (300 Mhz, DMSO-d$_6$) δ: 3.10 (m, 2H), 3.74 (m, 3H), 4.33 (s, 4H), 6.73 (s, br, 2H), 7.30 (s, br, 4H), 10.10 (s, br, 2H) [α]$_D^{25}$=−46.6 (c=1.0, MeOH)

EXAMPLE 4

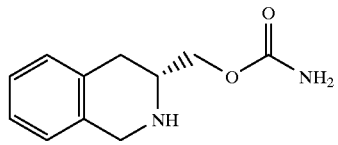

(R)-3-Carbamoyloxymethyl-1,2,3,4-tetrahydroisoquinoline

Starting from (R-3-hydroxymethyl-1,2,3,4-tetrahydroisoquinoline, the title product was prepared as the hydrochoride salt. Melting point 214–217° C.

EXAMPLE 5

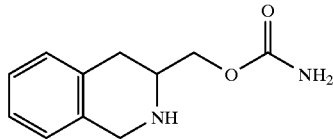

(S)-3-Carbamoyloxymethyl-1,2,3,4-tetrahydroisoquinoline

Starting with (RS)-3-hydroxymethyl-1,2,3,4-tetrahydroisoquinoline the title product was prepared as the hydrochloride salt. Melting point 203.7–204.3° C., $^1$H NMR (300 MHz, DMSO-d$_6$) δ: 3.01–3.16 (m, 2H), 3.43 (s, 1H), 4.12–4.35 (m, 4H), 6.69 (s, 2H), 7.12–7.36 (m, 4H), 10.04 (s, br, 2H).

EXAMPLE 6

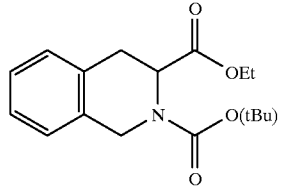

(RS)-N-tert-Butyloxycarbonyl-3-ethoxycarbonyl-1,2,3,4-tetrahydroisoquinoline

To 34 g of 1,2,3,4-tetrahydro-3-isoquinoline carboxylic acid, ethyl ester dissolved in 180 mL of the

EXAMPLE 7

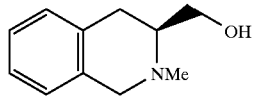

(S)-N-Methyl-3-hydroxymethyl-1,2,3,4-tetrahydroisoquinoline

To a solution of (S)-N-butyloxycarbonyl-3-ethoxycarbonyl-1,2,3,4-isoquinoline (12 g, 39.3 mmol) dissolved in 120 mL tetrahydrofuran, lithium aluminum hydride (4.7 g, 3.0 eq) was added carefully at 0° C. The reaction mixture was stirred 30 min at 0° C. and refluxed for 1 h. After cooling, reaction mixture was poured onto ice portion wise and the resulting solution was filtered over celite followed by 200 mL brine. The volatile component in the filtrate was evaporated in vacuo and the residue was extracted (dichloromethane, 200 mL×3). The combined organic layer was washed with brine and dried over MgSO$_4$ and concentrated. The residue was crystallized in Et$_2$O to afford 5.10 g (73.2%) of the product as white solid.

$^1$H-NMR (200 Mhz, CDCl$_3$) δ: 7.20–6.96 (m, 4H), 3.90–3.50 (m, 4H), 2.80 (m, 1H), 2.82–2.70 (m, 3H), 2.39 (3H)

EXAMPLE 8

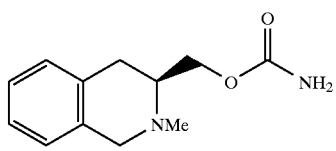

(S)-3-Carbamoyloxymethyl-N-methyl-1,2,3,4-tetrahydroisoquinoline

Starting with (S)-N-methyl-3-hydroxymethyl-1,2,3,4-tetrahydroisoquinoline the product was prepared as white solid.

$^1$H-NMR (300 MHz, DMSO-d$_6$) δ: 2.30 (s,3H), 2.68–2.95 (mn, 3H), 3.43–3.80 (m, 2H), 3.84–4.19 (m, 2H), 6.63–6.82 (m, 2H), 6.94–7.30 (m, 4H).
Product hydrochloride
$^1$H-NMR (300 Mhz, DMSO-d$_6$) δ: 2.64 (s, 3H), 2.70 (m, 2H), 2.92–3.16 (m, 2H), 3.91–4.41 (m, 4H), 6.76 (s, br, 2H), 7.00–7.35 (m, 4H).

EXAMPLE 9

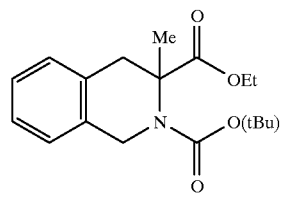

N-tert-Butyloxycarbonyl-3-ethoxycarbonyl-3-methyl-1,2,3,4-tetrahydroisoquinoline To 20g (65.5 mmol) of the N-tert-butyloxycarbonyl-3-ethoxycarbonyl-1,2,3,4-tetrahydroisoquinoline dissolved in anhydrous 150 mL tetrahydrofuran, potassium hexamethyldisilazine (KHMDS, 42.5 mL, 1.3 eq) was added at −78° C. under N$_2$ atmosphere. The reaction mixture was stirred for 30 min. and MeI (3.0 mL, 3.0 eq) was added at −78° C. and stirred for 30 min. at −78° C. and 3 h at room temperature.

The reaction mixture was poured onto 1N HCl (300 mL) and brine (600 mL) was followed. The volatile component were evaporated in vacuo then it was extracted with dichloromethane (300 mL×3) After evaporation of the solvent, the residue was dissolved in 250 mL of aq tetrahydrofuran (tetrahydrofuran:H$_2$O=3:1) and refluxed overnight in the presence of NaBH$_4$ (2.0 g) only to reduce the unmethylated starting material. The mixture was added to 1 N HCl (100 mL) and after evaporation of volatile, it was extracted with dichloromethane (200 mL×2), washed with brine (200 mL), concentrated and purified by column-chromatography (SiO$_2$, hexane:EtOAc=10:1) to afford the 18.7 g of the product (89.4%) as yellow liquid $^1$H-NMR (200 MHz, CDCl$_3$) δ: 7.30–6.95 (m, 4H), 4.73–4.54 (m, 1H), 4.42 (d, 1H), 4.32–3.95 (m, 2H), 3.13 (d, 1H), 2.79 (d, 1H), 1.45 (s, 9H), 1.41 (s, 3H), 1.20 (t, 3H)

EXAMPLE 10

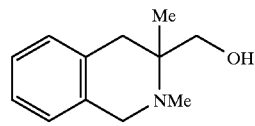

(RS)-3-Hydroxymethyl-3-methyl-N-methyl-1,2,3,4-tetrahydroisoquinoline

N-tert-Butyloxycarbonyl-3-ethoxycarbonyl-3-methyl-1,2,3,4-tetrahydroisoquinoline (10 g) was dissolved in 100 mL of tetrahydrofuran and lithium aluminum hydride (3.42g) was added carefully at 0° C. and the mixture was stirred for 30 min. Then, it was refluxed for 3 h and the reaction mixture was poured onto ice portion wise. The mixture was acidified to pH 1 by 2N HCl (2000 mL) and fltered over Celite 545. Volatile components in the resulting clear solution was evaporated in vacuo and after addition of 100 mL brine, it was extracted with dichloromethane (100 mL×3). Combined organic layer was dried over MgSO$_4$, filtered and concentrated to afford the product as yellow solid (5.98 g)

$^1$H-NMR (200 Mhz, CDCl$_3$) δ: 7.18–6.90 (m, 4H), 3.90 (d, 1H), 3.79 (d, 1H), 3.75 (d, 1H), 3.13 (d, 1H), 2.80 (bs, 1H), 2.34 (s, 3H), 0.94 (s, 3H)

--- dichloromethane, di-tert-butyl dicarbonate (37.9 g) was added to the solution portion wise. The reaction mixture was stirred for 30 min. until no gas evolution was observed. The mixture was washed with 200 mL 0.5N HCl solution followed by 200 mL brine. The organic layer was dried over MgSO$_4$ and evaporated in vacuo to provide 49.7 g (92%) of the product as yellow solid.

$^1$H-NMR (200 Mhz, CDCl$_3$) δ: 7.30–7.15 (bs, 4H), 5.10 (m, 1H), 4.80–4.45 (m, 2H), 4.20–4.00 (2H), 3.25–3.10 (m, 2H), 1.53 (s, 9H), 1.28 (t, 1H), 1.23 (t, 2H)

EXAMPLE 11

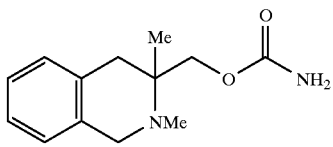

(RS-3-Carbamoyloxymethyl-3-methyl-N-methyl-1,2,3,4-tetrahydroisoquinoline

Starting with (RS)-3-hydroxymethyl-3-methyl-N-methyl-1,2,3,4-tetrahydroisoquinoline the product was obtained as white solid.

$^1$H-NMR (200 MHz, DMSO-d$_6$) δ: 7.38–7.20 (m, 4H), 6.77 (bs, 2H), 4.64–4.07 (m, 4H), 3.35–3.10 (m,2H), 2.90–2.73(m, 3H), 1.50 (s, 1H), 1.23 (s, 2H).

EXAMPLE 12

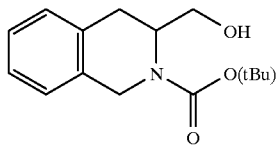

N-tert-Butyloxycarbonyl-3-hydroxymethyl-1,2,3,4-tetrahydroisoquinoline

The mixture of 3-hydroxymethyl-1,2,3,4-tetrahydroisoquinoline (13.9 g), 2-(t-butyloxycarbonyoxyimino)-2-phenylacetonitrile, triethylamine (10.4 mL) in tetrahydrofuran (150 mL) was stirred for 3 hours. The mixture was worked and chromatographed on silical gel to yield the product as yellow sticky oil (19.6 g).

$^1$H-NM (300 MHz, CDCl$_3$) δ: 1.49 (s, 9H), 1.97–2.13 (m, 2H), 3.06 (m, 1H), 3.51 (s, 2H), 4.294.94 (m, 3H, 7.00–7.27 (m, 4H).

EXAMPLE 13

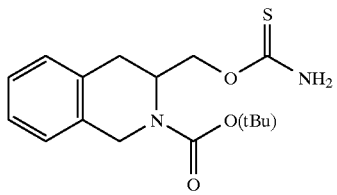

N-tert-Butyloxycarbonyl-3-thiocarbamoyloxymethyl-1,2,3,4-tetrahydroisoquinoline

To N-tert-Butyloxycarbonyl-3-hydroxymethyl-1,2,3,4-tetrahydroisoquinoline (9 g) dissolved in tetrahydrofuran (200 mL) at 0° C. was added sodium hydride (60% in mineral oil 1.64 g). The mixture wa stirred for 50 minutes then, carbon disulfide (2.5 mL) was added and stirred for an additional 1 hour. Then methyl iodide (2.55 mL) was added and after two hours ammonium hydroxide (28% solution, 10.4 mL) was added. After overnight stirring, brine was added, the mixture was extracted with methylene chloride and the extract concentrated to yield the product as a solid (5.6 g).

$^1$H-NMR (300 MHz, DMSO-d$_6$) δ: 1.41 (s, 9H), 2.75–2.98 (m, 1H), 3.00 (m, 1H), 4.10–4.41 (m, 4H), 7.18 (s, 4H), 8.46 (s, 1H), 8.82 (s, 1H).

EXAMPLE 14

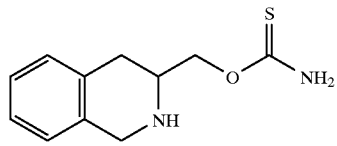

3-Thiocarbamoyloxymethyl-1,2,3,4-tetrahydroisoquinoline

To N-tert-butyloxycarbonyl-3-thiocarbamoyloxymethyl-1,2,3,4-tetrahydroisoquinoline (5.6 g) suspended in methanol (20 mL) was added 10 mL of 6 N HCl in methanol. After 6 hours, ether (30 mL) and isopropyl ether (10 mL) was added, the mixture was cooled to 0° C. and then filtered to yield the product as the hydrochloride salt (3 g). mp 167.6–168.2° C.

$^1$H-NMR (300 MHz, DMSO-d$_6$) δ: 2.85–3.11 (m, 2H), 3.74–3.95 (m, 1H), 4.20–4.38 (M, 1H), 4.45–4.62 (m, 1H), 7.02–7.39 (m, 4H), 8.92 (s, 1H), 9.10 (s, 1H), 9.66–10.1 (s, 1H).

EXAMPLE 15

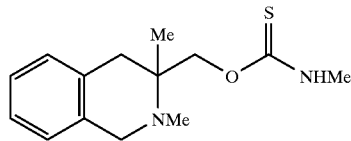

(RS)-N-Methyl-3-methyl-3-(N-Methylthiocarbamoyloxymethyl)-1,2,3,4-tetrahydroisoquinoline 25 mL dichloromethane solution containing 1.0 g (5.64 mmol) of the (RS)-3hydroxymethyl-3-methyl-N-methyl-1,2,3,4-tetrahydroisoquinoline was combined with NaH (60% in oil) at rt. The mixture was stirred for 15 minutes and MeNCS (495 mg, 1.2 eq) dissolved in 10 mL dichloromethane was added. The mixture was stirred for 2 hours and the reaction was quenched by addition of 1 N HCl. The mixture was basicified with sat. Na$_2$CO$_3$ (20 mL) and extracted with dichloromethane (50 mL×2). After evaporation and concentrated in vacuo, the residue was purified by column-chromatography (SiO$_2$, hexane:EtOAc=1:1.1). The product was dissolved in 30 mL tetrahydrofuran and treated with HCl methanol (0.5 N). Volatile components were evaporated in vacuo and the residue was washed with Et$_2$O (20 mL×2) to afford the product as yellow sticky gum.

$^1$H-NMR (200 Mhz, 60° C., DMSO-d$_6$) δ: 9.3 (bs, 1H), 7.36–7.12 (m, 4H), 4.75–4.25 (m, 5H), 3.05–2.65 (m, 7H), 2.55 (s, 1H), 1.35 (s, 2H)

EXAMPLE 16

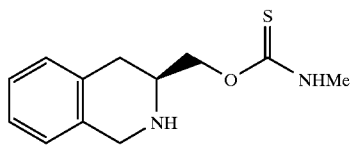

(S)-3-(N-Methylthiocarbamoyloxymethyl)-1,2,3,4-tetrahydroisoquinoline

To 50 mL dichloromethane solution containing (S)-3-hydroxymethy-1,2,3,4-tetrahydroisoquinoline (4.53 g, 27.75 mmol) was added di-tert-butyl dicarbonate (5.45 g, 25.0 mmol, 0.9 eq) and the reaction mixture was stirred for 2 hours until no gas bubbling was observed. The reaction mixture was washed with 0.5 N HCl (50 mL) followed by brine (50 mL) to remove the residual starting material. After drying wth MgSO$_4$ and filtration the, dichloromethane mixture was evaporated to yield crude (S)-N-tert-Butyloxycarbonyl-3-hydroxymethyl-1,2,3,4-tetrahydroisoquinoline. The crude N-tert-Butyloxycarbonyl-3-hydroxymethyl-1,2,3,4-tetrahydroisoquinoline was redissolved in 100 mL tetrahydrofuran. NaH (60%, 1.22 g) was added portion by portion to the solution at 0° C. and after 30 min stirring at room temperature, MeNCS (2.23 g) was added and the mixture was stirred for 2 h at rt. Brine (50 mL) was added to the mixture to quench the reaction and after evaporation of volatile component in vacuo, it was extracted with dichloromethane (50 mL×2) and combined layer was dried (MgSO$_4$), filtered, evaporated. The resulting material was chromatographed with hexane-EtOAc (4:1) mixture over SiO$_2$ to provide 7.07 g (81.8%) of (S)-N-tert-butyloxycarbonyl-3-(-Methyl-thiocarbamoyloxymethyl)-1,2,3,4tetrahydroisoquinoline. This material was dissolved in THF(30 mL) and 10 mL conc. HCl was added to the solution. One hour later, 5 mL of conc. HCl was added and stirred another 1 h until the reaction was finished. The reaction mixture was diluted with 30 mL of water and volatile components were evaporated. During the evaporation, desired product was precipitated as white solid. The solid was filtered and dried to yield the product as the hydrochloride salt (4.8 g).

$^1$H-NMR (200 MHz, DMSO-d$_6$) δ: 10.5–9.7 (m, 2H), 9.30 (s, 1H), 7.23 (s, 4H), 4.90 (m, 2H), 4.38 (s, 2H), 3.15–3.00 (m, 2H), 2.95 (d, 2H), 2.80 (1H)

EXAMPLE 17

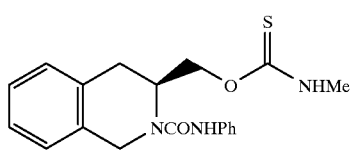

(S)-3-(N-Methyl-thiocarbamoyloxymethyl)-N-(anilinocarbonyl)-1,2,3,4-tetrahydroisoquinoline (S)-3-(N-Methyl-thiocarbamoyloxymethyl) -1,2,3,4-tetrahydroisoquinoline (1.0 g, 4.94 mmol) dissolved in 20 mL dichloromethane was combined with PhNCO (1.0 g) and stirred for 24 h at rt. The reaction mixture was evaporated and the crude product was purified by column-chromatography (SiO$_2$, hexanes:EtOAc=3:2) to provide the product as white solid (1.7 g).

$^1$H-NMR (200 MHz, CDCl$_3$) δ: 7.78 (s, 1H), 7.58–7.42 (m, 2H), 7.35–6.85 (m, 7H), 6.70 (s, 1H), 4.90–4.50 (m, 4H), 4.20–3.90 (m, 1H), 3.25–2.75 (m, 5H)

EXAMPLE 18

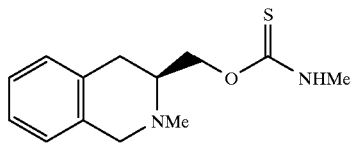

(S)-3-N-Methylthiocarbamoyloxymethyl)-N-methyl-1,2,3,4-tetrahydroisoquinoline (S)-N-Methyl-3-hydroxymethyl-1,2,3,4-tetrahydroisoquinoline (2.0 g, 11.3 mmol) was dissolved in 20 mL dichloromethane and NaH (60% in oil, 452 mg, 1.0 eq) was added at 0° C. and stirred for 30 min under N$_2$ atmosphere. MeNCS (850 mg, 1.03 eq) dissolved in 10 mL dichloromethane was then added to the reaction mixture and it was stirred overnight. The reaction mixture was evaporated and the residue was purified by column-chromatography (SiO$_2$, hex:EtOAc=1:2). The purified product was dissolved in Et$_2$O and acidified to pH=1 with 3N HCl. Th solvent was evaporated and the resulting white solid was washed with Et$_2$O (50 mL×3) to afford 2.4 g (74.4%) of the product.

$^1$H-NMR (200 Mhz, CDCl$_3$) δ: 7.17–6.90 (m, 4H), 6.70 (bs, 1H), 4.75–4.45(m, 2H), 3.86(d, 1H), 3.63 (d, 2H), 3.10–2.70 (m, 5H), 2.45 (s, 1H)

EXAMPLE 19

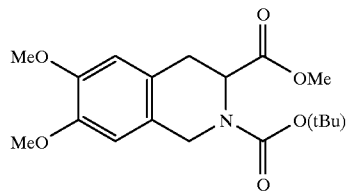

N-(t-Butyloxycarbonyl)-3-methoxycarbonyl-6,7-dimethoxy-1,2,3,4-tetrahydroisoquinoline To a suspension of O,O'-dimethyl-DOPA methyl ester (2.5 g, 9.1 mmol) in 35 mL of dichloromethane was added anhydrous formaldehyde in 15 mL dichloromethane followed by BF$_3$.Et$_2$O (836 μL,). The anhydrous formaldehyde was prepared by extraction of 2.5 mL aq formaldehyde with dichloromethane (5 mL×3) and subsequently drying over Na$_2$SO$_4$. The reaction mixture was refluxed overnight and the reaction mixture was poured into saturated Na$_2$CO$_3$ solution (30 mL) and extracted with dichioromethane (50 mL×3). The combined organic layer was dried over Na$_2$SO$_4$ and concentrated in vacuo. The residue was dissolved in 50 mL dichloromethane and stirred with 2.68 g of Boc$_2$O overnight. After evaporation of the volatile components in vacuo, the residue was purified by column-chromatography (SiO$_2$, hexane:EtOAc=2:1) to afford the product (2.5g, 75%)

$^1$H-NMR (200 Mhz, 60° C., CDCl$_3$) δ: 6.58 (s, 2H), 4.62 (d, 1H), 4.39 (d, 1H), 3.80 (s, 6H), 3.59 (s, 3H), 3.07 (r, 2H), 1.45 (s, 9H)

EXAMPLE 20

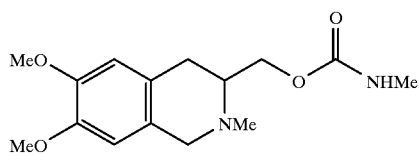

N-Methyl-3-(N-methylcarbamoyloxymethyl)-6,7-dimethoxy-1,2,3,4-tetrahydroisoquinoline N-(t-Butyloxycarbonyl)-3-methoxycarbonyl-6,7-dimethoxy-1,2,3,4-tetrahydroisoquinoline (1.77g, 4.8 mmol) dissolved in 48 mL tetrahydrofuran was combined with lithium aluminum hydride (231 mg, 1.25 eq) portionwise at 0° C. and the mixture was stirred for 75 minutes until the reaction is finished. The reaction mixture was poured onto ice and the mixture was filtered over celite. The volatile components in the filtrate was evaporated in vacuo and the resulting mixture was extracted with dichloromethane (50 mL×3) and dried over Na$_2$SO$_4$.

The combined organic layer was concentrated to 30 mL and carbonyl diimidazole (940 mg) was added to the mixture and stirred for 10 min, then MeNH$_2$ (10 mL) was added. After overnight stirring, the mixture was extracted with dichloromethane (30mL×3) after addition of 30 mL of brine, then dried over Na$_2$SO$_4$ and concentrated in vacuo. The residue was purified by column-chromaography (hex:EtOAc=3:1) to afford 1.44 g of the material. The BOC group of this material was deprotected by treatment by methanolic HCl to afford the product hydrochloride as pale yellow solid (0.80 g,)

$^1$H-NMR (200 Mhz, DMSO-d$_6$) δ: 9.80–9.45 (m, 2H), 7.05–7.03 (m, 1H), 6.85 (s, 1H), 6.80 (s, 1H), 4.434.15 (m, 5H), 3.80 (s, 6H), 2.98–2.82 (m, 2H), 2,62(d, 3H)

EXAMPLE 21

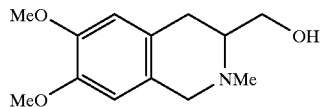

N-Methyl-3-hydroxymethyl-6,7-dimethoxy-1,2,3,4-tetrahydroisoquinoline

Following a method similar to that of Example 10, from N-(t-butyloxycarbonyl)-3-methoxycarbonyl-6,7-dimethoxy-1,2,3,4-tetrahydroisoquinoline starting material, the title product was obtained as the hydrochloride salt.

$^1$H-NMR (200 MHz, DMSO-d$_6$) δ: 6.85–6.75 (m, 2H), 4.50–4.05 (m, 3H), 3.95–3.37 (m, 10H), 3.20–2.85(m, 4H), 2.75–2.65 (m, 1H).

EXAMPLE 22

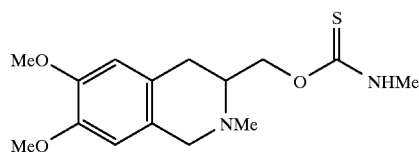

N-methyl-3-(N-methylthiocarbamoyloxymethyl)-6,7-dimethoxy-1,2,3,4-tetrahydroisoquinoline Starting from N-methyl-3-hydroxymethyl-6,7-dimethoxy-1,2,3,4-tetrahydroisoquinoline the title product was prepared as the hydrochloride salt.

$^1$H-NMR (200 Mhz, D$_2$O) δ: 6.85–6.73 (m, 2H), 4.85–4.50 (m, 3H), 4.50–4.05 (m, 2H), 3.73 (s, 6H), 3.20–2.75 (m, 7H), 2.60–2.45 (m, 1H).

What is claimed is:

1. A racemic or enantiomerically enriched compound represented by structural formula (I):

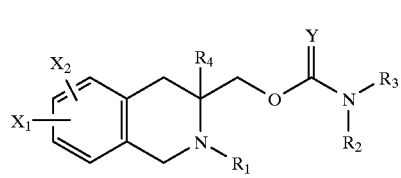

wherein:
X$_1$ and X$_2$ are the same or different from each other and independently represent a member selected from the group consisting of hydrogen, alkyl, alkoxy, thioalkoxy, halogen, hydroxy, nitro and trifluorocarbon;

Y is a member selected from the group consisting of oxygen and sulfur;

R$_1$ is a member selected from the group consisting of hydrogen, alkyl arylalkyl and CONHR' where R' is selected from the group consisting of hydrogen, alkyl, arylalkyl and aryl;

R$_2$ and R$_3$ are the same or different from each other and independently represent a member selected from the group consisting of hydrogen, alkyl, arylalkyl, and cycloalkyl, or R$_2$ and R$_3$ may form a 5 to 7-membered ring together with the nitrogen atom to which they are bonded;

R$_4$ is a member selected from the group consisting of hydrogen or lower alkyl;

and nontoxic pharmacologically acceptable salts thereof.

2. The compound of claim 1, wherein R$_1$ and R$_4$ are both hydrogen.

3. The compound of claim 1, wherein R$_1$, R$_4$, X$_1$ and X$_2$ are all hydrogen.

4. The compound of claim 1, wherein R$_1$, R$_2$, R$_3$, and R$_4$ are all hydrogen.

5. The compound of claim 1, wherein R$_1$ is hydrogen and X$_1$ and X$_2$ is a member selected from the group consisting of hydrogen, alkyl or halogen.

6. A pharmaceutical composition for treating disorders of the central nervous system which comprises as an active ingredient a therapeutically effective amount of a compound of claim 1 and a pharmaceutically acceptable carrier.

7. A method of treating a mammal suffering from disorder of the central nervous system which comprises administering to said mammal a central nervous system effective amount of the compound of claim 1.

8. The method according to claim 7 wherein the central nervous system disorder is depression.

9. A compound according to claim 1 represented by structural formula (II):

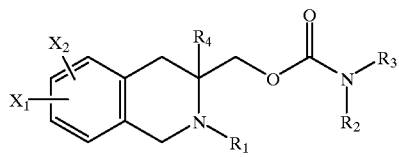

II wherein:

$X_1$ and $X_2$ are the same or different from each other and independently represent a member selected from the group consisting of hydrogen, alkyl alkoxy, thioalkoxy, halogen, hydroxy, nitro and trifluorocarbon;

$R_1$ is a member selected from the group consisting of hydrogen, alkyl, arylalkyl, and CONHR' where R' is selected from the group consisting of hydrogen, alkyl, arylalkyl and aryl;

$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;

$R_4$ is a member selected from the group consisting of hydrogen or lower alkyl;

and nontoxic pharmacologically acceptable salts thereof.

10. The compound of claim 9, wherein $R_1$ and $R_4$ are both hydrogen.

11. The compound of claim 9, wherein $R_1$, $R_4$, $X_1$ and $X_2$ are all hydrogen.

12. The compound of claim 9, wherein $R_1$, $R_2$, $R_3$, $R_4$ are all hydrogen.

13. A pharmaceutical composition for treating disorders of the central nervous system which comprises as an active ingredient a therapeutically effective amount of a compound of claim 10 and a pharmaceutically acceptable carrier.

14. A method of treating a mammal suffering from disorder of the central nervous system which comprises administering to said mammal a central nervous system effective amount of the compound of claim 9.

15. The method according to claim 14 wherein the central nervous system disorder is depression.

16. A compound according to claim 1 represented by structural formula (III):

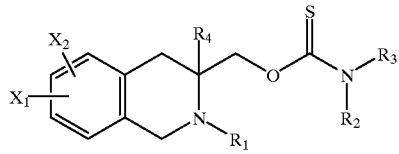

III wherein:

$X_1$ and $X_2$ are the same or different from each other and independently represent a member selected from the group consisting of hydrogen, alkyl alkoxy, thioalkoxy, halogen, hydroxy, nitro and trifluorocarbon;

$R_1$ is a member selected from the group consisting of hydrogen, alkyl, arylalkyl, and CONHR' where R' is selected from the group consisting of hydrogen, alkyl, arylalkyl and aryl;

$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded.

17. The compound of claim 16, wherein $R_1$ and $R_4$ are both hydrogen.

18. The compound of claim 16, wherein $R_1$, $R_4$, $X_1$ and $X_2$ are all hydrogen.

19. The compound of claim 16, wherein $R_1$, $R_2$, $R_3$, $R_4$ are all hydrogen.

20. A pharmaceutical composition for treating disorders of the central nervous system which comprises as an active ingredient a therapeutically effective amount of a compound of claim 16 and a pharmaceutically acceptable carrier.

21. A method of treating a mammal suffering from disorder of the central nervous system which comprises administering to said mammal a central nervous system effective amount of the compound of claim 16.

22. The method according to claim 21 wherein the central nervous system disorder is depression.

23. An enantiomerically enriched compound according to claim 1 represented by structural formula (IV):

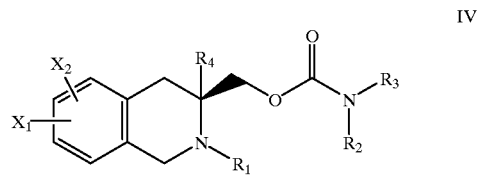

IV wherein:

$X_1$ and $X_2$ are the same or different from each other and independently represent a member selected from the group consisting of hydrogen, alkyl, alkoxy, thioalkoxy, halogen, hydroxy, nitro and trifluorocarbon, $R_1$ is a member selected from the group consisting of hydrogen, alkyl, arylalkyl, and CONHR' where R' is selected from the group consisting of hydrogen, alkyl, arylalkyl and aryl;

$R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;

$R_4$ is a member selected from the group consisting of hydrogen or lower alkyl;

and nontoxic pharmacologically acceptable salts thereof.

24. The compound of claim 23, wherein $R_1$ and $R_4$ are both hydrogen.

25. The compound of claim 23, wherein $R_1$, $R_4$, $X_1$ and $X_2$ are all hydrogen.

26. The compound of claim 23, wherein $R_1$, $R_2$, $R_3$, $R_4$ are all hydrogen.

27. The compound of claim 23, wherein $R_4$ is hydrogen, $X_1$ and $X_2$ is a member selected from the group consisting of hydrogen, alkyl or halogen.

28. A pharmaceutical composition for treating disorders of the central nervous system which comprises as an active ingredient a therapeutically effective amount of a compound of claim 23 and a pharmaceutically acceptable carrier.

29. A method of treating a mammal suffering from disorder of the central nervous system which comprises administering to said mammal a central nervous system effective amount of the compound of claim 23.

30. The method according to claim 29 wherein the central nervous system disorder is depression.

31. (S)-3-Carbamoyloxymethyl-1,2,3,4-tetrahydroisoquinoline and nontoxic pharmacologically acceptable salts thereof.

32. A pharmaceutical composition for treating disorders of the central nervous system which comprises as an active ingredient a therapeutically effective amount of a compound of claim 31 and a pharmaceutically acceptable carrier.

33. A method of treating a mammal suffering from disorder of the central nervous system which comprises administering to said mammal a central nervous system effective amount of the compound of claim 31.

34. The method according to claim 33 wherein the central nervous system disorder is depression.

35. An enantiomerically enriched compound according to claim 1 represented by structural formula (V):

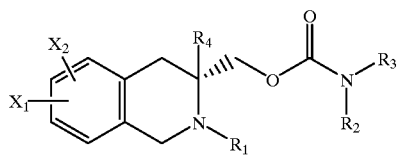

wherein:
- $X_1$ and $X_2$ are the same or different from each other and independently represent a member selected from the group consisting of hydrogen, alkyl, alkoxy, thioalkoxy, halogen, hydroxy, nitro and trifluorocarbon;
- $R_1$ is a member selected from the group consisting of hydrogen, alkyl arylalkyl, and CONHR" where R' is selected from the group consisting of hydrogen, alkyl, arylalkyl and aryl;
- $R_2$ and $R_3$ are the same or different from each other and independently represent a member selected from the group consisting of hydrogen, alkyl, arylalkyl, and cycloalkyl, or $R_2$ and $R_3$ may form a 5 to 7-membered ring together with the nitrogen atom to which they are bonded;
- $R_4$ is a member selected from the group consisting of hydrogen or lower alkyl;

and nontoxic pharmacologically acceptable salts thereof.

36. The compound of claim 35, wherein $R_1$ and $R_4$ are both hydrogen.

37. The compound of claim 35, wherein $R_1$, $R_4$, $X_1$ and $X_2$ are all hydrogen.

38. The compound of claim 35, wherein $R_1$, $R_2$, $R_3$, $R_4$ are all hydrogen.

39. A pharmaceutical composition for treating disorders of the central nervous system which comprises as an active ingredient a therapeutically effective amount of a compound of claim 35, and a pharmaceutically acceptable carrier.

40. A method of treating a mammal suffering from disorder of the central nervous system which comprises administering to said mammal a central nervous system effective amount of the compound of claim 35.

41. The method according to claim 40 wherein the central nervous system disorder is depression.

42. A compound selected from the group consisting of (S)-3-Carbamoyloxymethyl-1,2,3,4-tetrahydroisoquinoline, (R)-3-Carbamoyloxymethyl-1,2,3,4-tetrahydroisoquinoline and (RS)-3-Carbamoyloxymethyl-1,2,3,4-tetrahydroisoquinoline.

43. A method of treating a mammal suffering from disorder of the central nervous system which comprises administering to said mammal a central nervous system effective amount of the compound of claim 42.

44. The method according to claim 43 wherein the central nervous system disorder is depression.

45. An agent for treating diseases on which monoamine oxidase inhibition is effective comprising the compound of claim 1 as the active ingredient.

46. An agent for treating diseases on which monoamine oxidase inhibition is effective comprising the compound of claim 9 as the active ingredient.

47. An agent for treating diseases on which monoamine oxidase inhibition is effective comprising the compound of claim 23 as the active ingredient.

48. An agent for treating diseases on which monoamine oxidase inhibition is effective comprising the compound of claim 31 as the active ingredient.

49. An agent for treating diseases on which monoamine oxidase inhibition is effective comprising the compound of claim 35 as the active ingredient.

* * * * *